United States Patent [19]
Bruner

[11] Patent Number: 6,133,477
[45] Date of Patent: Oct. 17, 2000

[54] PREPARATION OF 3-PENTENOIC ACID

[75] Inventor: Harold Stanley Bruner, Hockessin, Del.

[73] Assignees: E. I. du Pont de Nemours and Company, Wilmington, Del.; DSM N.V., Netherlands

[21] Appl. No.: 09/120,990

[22] Filed: Jul. 23, 1998

Related U.S. Application Data

[60] Provisional application No. 60/053,534, Jul. 23, 1997.

[51] Int. Cl.$^7$ .............................. C07C 51/14; C07C 51/42
[52] U.S. Cl. ............................................ 562/522; 562/600
[58] Field of Search ....................... 562/522, 600

[56] References Cited

U.S. PATENT DOCUMENTS

| | | | |
|---|---|---|---|
| 3,579,551 | 5/1971 | Craddock et al. | 260/413 |
| 3,579,552 | 5/1971 | Craddock et al. | 260/413 |
| 3,887,489 | 6/1975 | Fannin et al. | |
| 4,381,221 | 4/1983 | Isshiki et al. | 203/6 |
| 4,622,423 | 11/1986 | Burke | 562/522 |
| 4,690,912 | 9/1987 | Paulik et al. | 502/161 |
| 4,792,620 | 12/1988 | Paulik et al. | 560/232 |
| 5,003,104 | 3/1991 | Paulik et al. | 562/517 |
| 5,145,995 | 9/1992 | Burke | 562/522 |
| 5,166,421 | 11/1992 | Bruner, Jr. | 562/522 |
| 5,227,520 | 7/1993 | Cooper | 562/519 |
| 5,237,097 | 8/1993 | Smith et al. | 562/519 |
| 5,250,726 | 10/1993 | Burke | 562/522 |
| 5,359,137 | 10/1994 | Burke | 562/517 |

FOREIGN PATENT DOCUMENTS

WO 96/14287  5/1996  WIPO .................... C07C 51/12

*Primary Examiner*—Gary Geist
*Assistant Examiner*—Robert W. Deemie

[57] ABSTRACT

An improved process for the preparation of 3-pentenoic acid by reaction of butadiene with carbon monoxide and water in the presence of a rhodium-containing catalyst and an iodide promoter where carbon monoxide stripping is employed to separate and recover the 3-pentenoic acid product.

10 Claims, 1 Drawing Sheet

PREPARATION OF 3-PENTENOIC ACID

CROSS-REFERENCE TO RELATED APPLICATIONS

Applicants claim the benefit of priority to provisional application 60/053,534 filed Jul. 23, 1997.

STATEMENT REGARDING FEDERALLY SPONSORED RESEARCH OR DEVELOPMENT

"Not Applicable"

BACKGROUND OF THE INVENTION

1. Field of the Invention

This invention relates to a process for the preparation of 3-pentenoic acid by reacting butadiene with carbon monoxide and water in the presence of a rhodium-containing catalyst and an iodide promoter. More specifically but not by way of limitation, the invention relates to an improved method of isolating and recovering 3-pentenoic acid involving the use of carbon monoxide to vaporize the 3-pentenoic acid.

2. Description of the Prior Art

Numerous patents address the hydrocarboxylation of butadiene to 3-pentenoic acid. U.S. Pat. No. 5,250,726 details the reaction of butadiene with carbon monoxide and water in a carboxylic acid solvent in the presence of a rhodium catalyst, an iodide promoter, and a sulphonic acid catalyst. U.S. Pat. No. 5,145,995 claims a process which reacts butadiene with carbon monoxide and water in a carboxylic acid solvent in the presence of rhodium and an iodide or bromide promoter. U.S. Pat. No. 4,622,423 discloses a process for the preparation of 3-pentenoic acid by hydrocarboxylating butadiene with carbon monoxide and water in the presence of a rhodium-containing catalyst, an iodide promoter and certain inert halocarbon solvents. U.S. Pat. No. 4,690,912 claims a catalyst system for carboxylation reactions which consists of rhodium and an iodide containing promoter.

U.S. Pat. No. 5,227,520 discloses a process for purifying an iodide-contaminated carboxylic acid product from an iodide promoted carboxylation which comprises vaporizing the carboxylic acid to free it of catalyst, feedstock, and promoter wherein the vaporized carboxylic acid has a reduced iodide contamination.

U.S. Pat. No. 5,237,097 claims a carbonylation process where the product solution is conveyed to a separation zone where in the presence of carbon monoxide, the product is distilled. In the process, the absolute temperature and pressure in the separation zone is lower than in the reaction zone.

PCT Application WO96/14287 discloses a process for preparing carboxylic acids where following reaction the product is separated from the catalyst by vaporization. Following separation, the non-volatilized portion is placed in contact with carbon monoxide prior to being returned to the reaction zone. The exposure to carbon monoxide is done in a manner which does not allow carbon monoxide to return to the separation zone.

BRIEF SUMMARY OF THE INVENTION

The present invention provides a process for the preparation of 3-pentenoic acid by reaction of butadiene with carbon monoxide and water in the presence of a rhodium-containing catalyst and an iodide promoter where the improvement comprises recovery of the 3-pentenoic acid from the reaction product by vaporization of 3-pentenoic acid by bubbling carbon monoxide through the reaction product at a temperature of from 120° C. to 220° C. and condensing 3-pentenoic acid contained in the offgas. The carbon monoxide can be recycled back to the process. Optionally, a ligand which is capable of coordinating with rhodium is present in the reaction mixture. This ligand may be, for example, triphenylphosphine oxide or diphenylsulfoxide. To reduce rhodium triiodide precipitation during the carbon monoxide stripping, a water wash prior to carbon monoxide addition may be advantageously employed. Also, regeneration of the rhodium in the recycle loop may be accomplished at elevated temperature and elevated pressure.

DETAILED DESCRIPTION OF INVENTION

Figure 1:
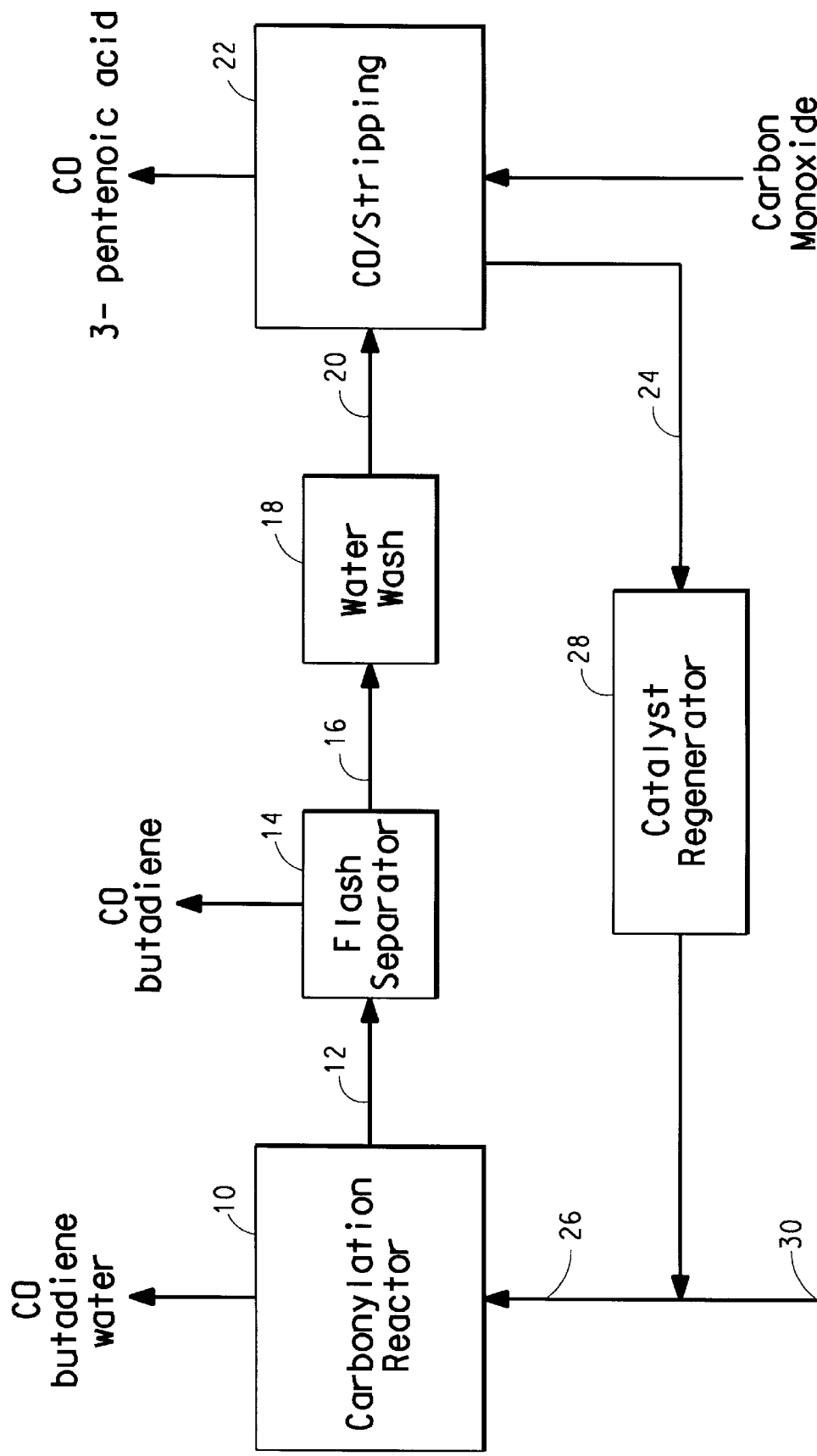
FIG. 1 is a schematic block diagram of one embodiment of the improve process according to the present invention illustrating a carbonylation reactor, an intermediate flash recovery unit, an optional water wash unit prior to the carbon monoxide stripping unit and a rhodium regeneration unit in the recycle loop.

The improved process for manufacturing 3-pentenoic acid according to the present invention, how the carbon monoxide stripping step is incorporated into the overall process, and the advantages/benefits of this improvement can perhaps be best explained and understood by reference to the drawing. FIG. 1 illustrates schematically one particularly preferred embodiment of the improved process wherein a carbonylation reactor 10 is employed to react butadiene, carbon monoxide and water using a rhodium catalyst at elevated temperature and pressure. The reaction product stream exiting the carbonylation reactor 10 via line 12 is flashed in vessel 14 to remove unreacted gaseous CO and butadiene. These reactants are then recycled (not shown in the figure) along with make-up reactants to the carbonylation reactor 10. In this specific embodiment the product stream from the flash vessel 14 is delivered via line 16 to an optional water wash unit 18 before entering via line 20 a carbon monoxide stripping vessel 22. Within this vessel 22, the 3-pentenoic acid is vaporized and swept overhead by the CO gaseous phase being introduced at the bottom of the vessel 22. The remaining product solution containing the rhodium catalyst and catalyst promoters is then recycled via lines 24 and 26 to the carbonylation reactor 10. A catalyst regenerator 28 and purge line 30 are provided in this recycle loop to regenerate the desired rhodium complex and to control the build-up of high boilers, respectively.

The catalyst precursor useful in the carbonylation reaction can be any rhodium complex that is free of interfering ligands, particularly bidentate phosphine and nitrogen ligands. Examples include rhodium (III) iodide, rhodium (II) acetate dimer, rhodium (I) dicarbonyliodide dimer, acetylacetonatodicarbonylrhodium (I), chlorodicarbonylrhodium (I), and tris(acetylacetonato)rhodium (III). The specific rhodium concentration to be employed is not critical but is usually in the range of 0.01 to 0.6% by weight. Generally a higher rhodium concentration increases the reaction rate in the synthesis, but reduces stability in distillation and increases yield loss to six carbon dibasic acids. The most preferable range is from 0.02 to 0.30% by weight.

The catalyst, which can be either preformed or formed in situ, must be promoted with the addition of iodide to achieve a satisfactory reaction rate. Hydrogen iodide (HI) is the preferred source of iodide, but an alkyl iodide having 1 to 10 carbons is also a suitable source. 2-Iodobutane is already reversibly formed in the process from the reaction of butene byproducts and hydrogen iodide and is therefore an especially good alkyl iodide source. Generally, the concentration of iodide is between 0.05 and 1.0% by weight, but the absolute weight of iodide is less important than the molar ratio of iodide to rhodium (I/Rh). The I/Rh ratio is normally 1 to 3 and preferably 1 to 2. Higher I/Rh ratios tend to be less selective in the synthesis and have decreased stability in the distillation. A I/Rh ratio of less than 1 has a lower catalyst activity and reduced stability during synthesis.

In order for this process to maintain activity in synthesis, it is also necessary to adjust the total concentration of the iodide promoter to allow for the natural equilibrium between butenes that are formed as a byproduct and the promoter. In the case of HI promoter, butenes and HI reversibly react to form 2-iodobutane. The excess iodide is maintained both by recycling 2-iodobutane formed in the synthesis step back to the reaction and by adding fresh iodide.

Temperatures of 100 to 220° C. can be used for this reaction, but best rates and yields are achieved between 100 to 160° C. Above 160° C., yields to 3-pentenoic acid are reduced. Below 100° C., reaction rates become too slow for practical commercial exploitation.

The reaction is actually accelerated and made more selective by lower pressures down to a relatively low range. The chemistry will proceed over the range of 5 to 200 atmospheres but 10 to 75 atmospheres are preferred.

In order to minimize process complexity, the preferred solvent for a commercial process is the mixture of acid byproducts that are less volatile than 3-pentenoic acid. These are mostly six carbon diacids (adipic acid, 2-methylglutaric acid, and 2-ethylsuccinic acid) and saturated and unsaturated nine carbon acids (e.g., nonanoic acid or cyclohexylproprionic acid). However, any organic acid, diacid or polyacid of 2 to 20 carbons could be used. The more polar acids, especially the diacids, increase the stability of the rhodium catalyst during pentenoic acid distillation.

While not wanting to be limited by any particular theory, it is believed that the rhodium catalyst shifts between the +1 and +3 oxidation steps during the course of the synthesis. It is further believed that the rhodium complexes lose carbon monoxide (CO) causing the rhodium +3 to precipitate during distillation. Recovery of 3-pentenoic acid without rhodium loss requires the highest CO partial pressure be present that will allow removal of the 3-pentenoic acid at the minimum holdup time during distillation. Within the bounds discussed above, lower iodide/rhodium ratio, lower total rhodium concentration, and higher CO pressure, improve catalyst stability during distillation.

The product from the carbonylation reactor may be passed directly to a still for separation of the product from the catalyst and high boiler impurities. CO stripping is the preferred method for recovering the 3-pentenoic acid from the catalyst solution. CO is bubbled through the mixture and 3-pentenoic acid is condensed from the offgas. CO is then recycled back to the process. To minimize the time that rhodium is exposed to low CO and high temperature, engineering equipment which greatly increase the CO/liquid surface area (for example, falling film evaporator) may be advantageously used.

Higher temperatures will increase the vapor pressure of 3-pentenoic acid and make the stripping more efficient, but will also destabilize the rhodium more rapidly. Temperatures can be in the range of 120 to 220° C., preferably 140 to 190° C. and more preferably 140 to 160°. Most preferably, the temperature used for CO stripping is equal to or above that used in the carbonylation reactor.

Higher pressures for the CO stripping increase the stability of the rhodium at a given temperature, but increase the number of moles of CO that must be recycled and recompressed per mole of 3-pentenoic acid recovered. At very high CO pressures, a greater portion of the rhodium (+1) complex $(Rh(CO)_3I)$ is present relative to the dimer $[Rh_2(CO)_4I_2]$. Since the monomer is more volatile, the higher pressure may further complicate 3-pentenoic acid recovery. The stripping may be run from 10 mm of Hg vacuum to 50 atmospheres of pressure, however, it is more economically done at or below atmospheric pressure. For pressures near atmospheric pressure, a temperature of 140 to 160° C. is preferred.

The remaining product solution, containing the catalyst, from the CO stripper can be recycled to the carbonylation reactor. A portion of this product solution may be purged from the system to reduce high boiler build-up.

The use of a ligand which can coordinate with rhodium increases the stability of the rhodium catalyst during 3-pentenoic acid recovery. Ideally, such a ligand is able to coordinate to the rhodium when both butadiene and CO are quite low but, but at the same time, be readily replaced by these species when the catalyst is returned to the synthesis step. As previously discussed, the byproduct six carbon diacids or the more polar monoacids are thought to improve the stability by acting as these ligands. Other ligands may be more effective. These ligands include triarylphosphine oxides (such as triphenylphosphine oxide) and diphenylsulfoxide. The optimum level of ligand stabilizer will vary with the ligand, but the maximum stability improvement is generally achieved at a ligand/rhodium ratio of 5 to 15.

Optionally, a first stripper which removes unreacted CO and butadiene from the carbonylation reactor is placed after the carbonylation reactor and before the still used for separation of the pentenoic acid product from the catalyst. The CO and butadiene may be recycled to the carbonylation reactor.

The amount of water present is important in determining the final Rh(+1)/Rh(+3) ratio in the catalyst. Large excesses of water relative to butadiene in synthesis (for example above 1.5), may increase the Rh(+1)/Rh(+3) ratio leaving synthesis but have a detrimental effect on 3-pentenoic acid yield and CO consumption. However, water is useful in stabilizing rhodium during distillation. As such, water can optionally be added after synthesis and before isolation of the product. Amounts of water up to 35% of the total solvent have been tested with good results in the CO stripper.

The rhodium catalyst and the HI may react either prior to or during the stripping step to produce rhodium triiodide which precipitates in the stripper. This problem becomes more severe as the I/Rh ratio in the catalyst mixture is increased. A water washing and decanting step may optionally be added between the synthesis and the stripping steps, preferably after the inerts flash (stream 16 of FIG. 1). This wash step hydrolyzes the organoiodides that form during the synthesis step, liberates HI by converting the various rhodium complexes present to neutral complexes, and finally removes the HI to the aqueous phase for decantation to prevent it from being fed to the stripper. The aqueous phase from the decantation may be fed back to synthesis as all or part of the water feed to that unit and/or be used as a purge of dibasic acids which are preferentially soluble in water relative to 3-pentenoic acid.

The quantity of water required will vary depending on the solution composition and the wash temperature, but should be sufficient to produce an aqueous phase exiting the decanter that is at least 1 to 5 wt % of the organic phase. Although the wash can be effective even at 20° C., the cost of cooling and re-heating the stream between the 100–160° C. synthesis step and the 140–160° C. stripping step would make the treatment overly expensive to implement. It is, therefore, contemplated that the wash will be run at a temperature intermediate to the two steps.

Dimers and oligomers of butadiene, formed as byproducts in the synthesis step, can react with a small fraction of the rhodium catalyst to form a complex that is not very catalytically active and also reversibly add HI to reduce the available concentration of the co-catalyst. Although this loss in activity can be mediated by the recovery and re-addition of rhodium and iodide from the purge, optimum activity is preferentially maintained by subjecting all or part of the recycling catalyst stream after 3-pentenoic acid recovery to a catalyst reactivation step (e.g., see stream 26 and regeneration unit 28 of FIG. 1).

The regeneration step converts the carbon double bonds by hydrogenation and hydrocarboxylation, thereby removing them as potential ligands. It is contemplated that this step is to be run for 1 to 3 hours at 180 to 200° C., and 100 to 1,000 psig (6.8 to 68 bar) of either CO or CO/hydrogen mixtures, with enough water added to create a 1 to 5% water concentration.

The following example further illustrates various aspects and feature of the overall improved process according to the present invention and as such is not intended to be unduly limiting.

EXAMPLE 1

Rh/I Catalyzed Hydrocarboxylation Followed By Atmospheric CO Stripping of 3-Pentenoic Acid Product Step 1: Reaction;

Catalyst solution was prepared with the following recipe: 1436.0 grams nonanoic acid, 2.2 grams rhodium dicarbonyl acetyl acetoate (acac), and 3.76 grams aqueous (54%) hydriodic acid (HI). The mixture was stirred and sparged with carbon monoxide until dissolved. Half of this solution was charged to a 1 liter Hastelloy C276 autoclave which is equipped with a stirrer. The solution was stirred at 1500 rpm and heated rapidly to 140° C. liquid temperature, under 350 psig carbon monoxide pressure. When temperature was reached, liquid feed was introduced to the reactor from 2 syringe pumps, 1 feeding 1,3 Butadiene at 50 ml/hr, the other feeding water at 19 ml/hr (slight excess water). Feed was continued until 1 hour had elapsed, approximately 5% by weight butadiene had been fed. The reactor was pressured to 500 psig during the feed hour and left open to a regulated CO supply with uptake reader. The batch reaction was continued until uptake slowed to less than 20 SCCM. The reactor was then cooled and vented of CO pressure and the liquid drained into a product bottle. The second half of the catalyst mixture was then charged to the autoclave and the above reaction sequence was repeated to yield a total of nearly 1700 ml product solution consisting of over 90 wt % nonanoic acid, with 7.5 wt % 3-Pentenoic Acid and unreacted butadiene and water each less than 1 wt %.

Step 2: Product Recovery;

300 grams of 3-Pentenoic Acid is added to the product solution from step 1 above to facilitate an easier separation via distillation. The resulting feed solution for stripping is 23.5 wt % 3-pentenoic acid, 76.0 wt % nonanoic acid, and 0.5 wt % water. The stripper column is a glass 25 mm diameter Oldershaw type column with 35 plates, with the feed introduced 5 plates from the bottom (ie. 30 plates of rectification). The column is jacketed with boiling mesitylene under slight vacuum (162° C.) for heating the liquid on all 35 trays. Carbon monoxide is fed to the column at 1.1 bar, 10.0 SLPM, as a stripping gas. The use of carbon monoxide helps control temperatures in the column and stabilizes the rhodium catalyst for precipitation. The feed solution is fed to the column at 8.7 grams per minute with a rhodium concentration of 414 ppm, and an iodide concentration of 907 ppm. The liquid temperature in the column varied on each plate between 135 and 155° C. The large majority of the overhead material, after condensing, was returned to the top of the column as reflux. The ratio of liquid fed to the top of the column to distillate taken off the top of the column was 15:1. The overhead was taken off at 1.12 grams per minute at a composition of 99.5 wt % 3-pentenoic acid, 0.5 wt % water, 0.30 ppm Rh and 441 ppm iodide. The large number of plates and high reflux ratio are necessary for near complete removal of rhodium from the overhead stream. The bottoms composition was 11.5 wt % 3-Pentenoic Acid, with the remainder primarily nonanoic acid. The bottoms rhodium and iodide levels were 508 and 882 ppm respectively.

EXAMPLE 2

Rh/I Catalyzed Hydrocarboxylation Followed By Vacuum CO Stripping of 3-Pentenoic Acid Product 2,000 grams of catalyst feed material was made in heptanoic acid solvent. The solution contained 1 wt % water, 400 ppm Rh as Rh dicarbonyl acac, and HI added at a 1.8:1 molar ratio to Rh. This material was fed continuously to a 1 liter reactor (1 hour hold up time) under 500 psig CO pressure and 140° C. The stream exiting the reactor was then flashed to 15 psig CO pressure (with a total condenser) in a tube with 10 minutes hold up time. This material was then fed at 12 grams per minute to a 35 plate, 1 inch diameter Oldershaw column at the 5th tray from the bottom. The column was fully jacketed with boiling decane under vacuum at 160° C. and was swept with CO flow of 7,500 SCCM. The tails of this stripper was then collected and recycled continuously to the 1 liter reactor. Shortly after startup of the stripper column, black solids began to form on the glass column, later analyzed as having a 3:1 I/Rh molar ratio. 5 wt % 1,3 butadiene feed was begun to the reactor along with HI/water feed at 0.6 $H_2O$ to butadiene ratio and 0.7 HI/Rh ratio. At the same time the exit stream of the reactor was fed with 10 wt % water. The overhead of the stripper was therefore primarily water which prevented the HI/water azeotrope from coming overhead. As a result the iodide/Rh ratio rapidly rose upon recycle. The material was recycled with product 3-pentenoic acid and excess water removed as overhead product in the stripper and a nearly constant system inventory maintained. The column continued to blacken severely for 24 hours and the unit was shut down for draining and cleaning.

The resulting catalyst mixture of 1,900 grams prior to water washing (mostly heptanoic acid, water, small levels of 3-pentenoic acid and dibasic acids) had what appeared to be a small aqueous phase at the bottom. 50 grams of water was added to this mixture to improve extraction of HI into the water phase. The mixture was stirred under CO for 1 hour. The resulting two phase mixture was then left to settle for 12 hours prior to decanting. The aqueous phase was then removed from the mixture and both phases were analyzed.

The glass stripper column was cleaned with a butyl amine/butanol boilup which dissolved the black solids. The column was then rinsed with boiling acetone three times and blown dry. The organic phase from the above water wash was fed back to the unit. The unit was then restarted under the same conditions as before except without butadiene, water or HI feed. The unit ran in total recycle at 12 grams per minute stripper feed rate with 0.7 g/min overheads flowing back to the tails vessel, 161° C. jacket temperature, and 6500 cc/min CO. There was a very slight amount of grayness added to the glass in 15 hours time, a major improvement from the solids deposition seen in the first portion of the experiment.

EXAMPLE 3

Rh/I Catalyzed Hydrocarboxylation Followed By Atmospheric CO Stripping of 3-Pentenoic Acid Product With and Without Water Wash Under a CO atmosphere, 1.01 grams of $Rh(acac)(CO)_2$ were slurried in 40 grams of acetic acid and then 2.18 grams of 57% aqueous HI were added to produce a clear, dark-red solution. This was then added to 750 grams of nonanoic acid to form a feed solution that was 500 ppm rhodium, with an I/Rh ratio of 2.5. This solution was fed at 0.5 cc/minute to a 100 cc Parr autoclave operating at 1,000 rpm at 140° C. and 500 psig (34 bar) with a level control to give a two hour residence time for the liquid. Butadiene and water were also fed at 0.27 g/min and 0.11 g/min respectively. CO was fed at 27 sccm. About half the product of this reaction, now about 4.2% 3-pentenoic acid, was washed with 5% of its weight of water at 25° C., recovering an aqueous phase after decantation of 2.6% of the organic phase. The I/Rh ratio in the washed stream was reduced to 2.0 while the rhodium concentration was reduced only 5%.

Both the washed and the unwashed products were then subjected to a stability test where 25 cc of feed was heated for 30 minutes at temperature with 50 cc/minute of CO bubbled through at 1 atmosphere. The temperatures were increased until solids formation was observed. The unwashed material formed $RhI_3$ solids at 100° C. The washed material formed $RhI_3$ solids at 150° C.

EXAMPLE 4

Catalyst Regeneration

A fresh catalyst solution was prepared as follows. Acetic acid (15.0 gm), deionized water (10.7 gm), and n-butylbenzene (1.00 gm, internal GC standard) were added to a septum bottle then degassed with carbon monoxide. $Rh(CO)_2(CH_3COCHCOCH_3)$ (0.402 gm, 1.56 mmol) was quickly added to the acetic acid solution followed by 57% aqueous hydriodic acid (1.16 gm, 5.2 mmol). Stirring under carbon monoxide was continued until all the solids dissolved. The active catalyst solution was diluted with acetic acid (71.7 gm) which had been degassed with carbon monoxide.

Under a carbon monoxide atmosphere, the catalyst solution was added to an Hastelloy B2 autoclave equipped with a high-pressure infrared cell. With 1000 rpm stirring, the carbon monoxide pressure was increased to 350 psig then the solution was heated to 140° C. At this temperature, the total pressure was adjusted to 500 psig. An in-situ infrared measurement indicated that an active catalyst species, $H^+[Rh(CO)_2I_2]^-$, was the only detectable solution species. 1,3-Butadiene (33.5 gm, 0.62 mol, 25 wt %) was then added to the reactor over a three-minute period and the reactor conditions were held between 140 to 142° C. and 500 to 750 psig total pressure for another four hours. Within 30 minutes, the infrared measurements showed complete disappearance of active rhodium species and the appearance of an unidentified species with a single rhodium carbonyl absorption at 2,065 $cm^{-1}$. At the end of this reaction period, a liquid sample was collected and analyzed for water (7.7 wt %) and organic products by gas chromatography. Only 0.08 mole of cis and trans 3-pentenoic acid had been produced with no detectable C6 dibasic acid formation (2-ethylsuccinic, 2-methylglutaric, and adipic acids). All of these observations were consistent with complete catalyst deactivation by the high butadiene exposure.

With 1,000 rpm stirring, the deactivated catalyst solution was cooled to 65° C. and pressure-purged (cycling between 500 and 100 psig) fifteen times with fresh carbon monoxide feed to vent unreacted butadiene from the reactor. The resulting catalyst solution was pressurized to 300 psig then heated over a two-hour period to 182° C. and the total pressure was adjusted to 500 psig with carbon monoxide feed. Infrared measurements over a six-hour period (182° C., 500 psig) showed the inactive rhodium species (2065 $cm^{-1}$) being converted to the active species, $H^+[Rh(CO)_2I_2]^-$ and $[Rh(CO)_2I]_2$, and the formation of active water-gas-shift catalysts (carbon dioxide formation). At the end of this regeneration period, a liquid sample was collected from the reactor and analyzed for water (1.6 wt %) and organic products by gas chromatography. The 3-pentenoic acid produced from butadiene prior to catalyst deactivation had been completely converted to the C6 dibasic acids listed above and gamma-valerolactone indicating monoolefin hydrocarboxylation activity. All of these observations are consistent with regeneration of the rhodium iodide catalyst deactivated by butadiene in the previous reaction step.

With 1,000 rpm stirring, the resulting catalyst solution was cooled to 65° C. then pressure-purged (cycling between 500 and 100 psig) ten times with fresh carbon monoxide feed to remove water-gas-shift gases (carbon dioxide and hydrogen) from the reactor. Deionized water (6 ml) was added to the catalyst solution and the reactor pressure increased to 300 psig with carbon monoxide. After heating to 140° C., the reactor pressure was adjusted to 500 psig then 1,3-butadiene (10.0 gm, 0.185 mol, 10 wt %) was added to the reactor over a one-minute period. The reactor conditions were held between 138 to 142° C. and 500 to 750 psig total pressure for two hours. Semibatch carbon monoxide feed to the reactor was necessary to prevent the pressure from falling below 500 psig. Liquid samples which were collected as a function of time showed evidence of an active butadiene hydrocarboxylation catalyst. The 3-pentenoic acid concentration reached a maximum of 17.0 wt % (0.17 mol, 92% theoretical butadiene conversion) at 30 minutes after butadiene feed. The catalyst was still active at high butadiene conversion as shown by the conversion of the 3-pentenoic acid product to C6 dibasic acids at longer reaction times. Infrared measurements during this butadiene hydrocarboxylation reaction were also consistent with this conclusion as rhodium carbonyl bands for active $H^+[Rh(CO)_2I_2]^{31}$ and $[Rh(CO)_2I]_2$ were observed throughout the experiment.

Having thus described and exemplified the invention with a certain degree of particularity, it should be appreciated that the following claims are not to be so limited but are to be afforded a scope commensurate with the wording of each element of the claim and equivalents thereof.

I claim:

1. In a process for the preparation of 3-pentenoic acid by reacting butadiene with carbon monoxide and water in the presence of a rhodium-containing catalyst and an iodide promoter and then recovering of the 3-pentenoic acid from the reaction product wherein the improvement comprises the steps of:

(a) vaporizing 3-pentenoic acid by passing carbon monoxide through the reaction product at a temperature of from 120° C. to 220° C.;

(b) isolating and condensing the 3-pentenoic acid vaporized in step a and;

(c) isolating and recycling the carbon monoxide gas back to step (a).

2. The process of claim 1 further comprising the step of: water washing the reaction product prior to vaporizing 3-pentenoic acid such as to reduce the precipitation of rhodium trioxide during the carbon monoxide stripping step (a).

3. The process of claim 1 further comprising the step of: recovering the catalyst containing residue remaining after vaporizing 3-penenoic acid with carbon monoxide in step (a) and subjecting this residue to 1 to 3 hours at 180 to 200° C. and 100 to 1,000 psig hydrogen, carbon monoxide or mixtures thereof in the presence of 1 to 5 wt % water such as to regenerate the catalyst.

4. The process of claim 1 wherein step (a) is performed at 140° C. to 160° C.

5. In a process for the preparation of 3-pentenoic acid by the steps of reacting butadiene with carbon monoxide and water in the presence of a rhodium-containing catalyst and an iodide promoter and then recovering the 3-pentenoic acid from the reaction product wherein the improvement comprises the steps of:

(a) separating carbon monoxide and butadiene from the reaction product by vaporization, (b) vaporizing 3-pentenoic acid by passing carbon monoxide through the reaction product at a temperature of from 140° C. to 160° C.

(c) isolating and condensing the 3-pentenoic acid vaporized in step (b) and (d) isolating and recycling the carbon monoxide gas back to step (b).

6. The process of claim 5 further comprising the step of: water washing the reaction product prior to vaporizing 3-pentenoic acid such as to reduce the precipitation of rhodium trioxide during the carbon monoxide stripping step (b).

7. The process of claim 5 further comprising the step of: recovering the catalyst containing residue remaining after vaporizing 3-penenoic acid with carbon monoxide in step (b) and subjecting this residue to 1 to 3 hours at 180 to 200° C. and 100 to 1,000 psig hydrogen, carbon monoxide or mixtures thereof in the presence of 1 to 5 wt % water such as to regenerate the catalyst.

8. The process as in any one of claims 1–7 wherein a ligand capable of coordinating with rhodium is present in the reaction product.

9. The process of claim 8 wherein the ligand is chosen from the group consisting of a triarylphospine oxide or diphenylsulfoxide.

10. The process of claim 8 wherein the ligand is triphenylphosphine oxide.

* * * * *